United States Patent
Dihora et al.

(10) Patent No.: US 12,187,829 B2
(45) Date of Patent: Jan. 7, 2025

(54) ENVIRONMENTALLY BIODEGRADABLE MICROCAPSULES

(71) Applicant: TRUCAPSOL LLC, Bethlehem, PA (US)

(72) Inventors: Jiten Dihora, Center Valley, PA (US); Stephen Crescimanno, Hatfield, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 30 days.

(21) Appl. No.: 17/861,204

(22) Filed: Jul. 9, 2022

(65) Prior Publication Data

US 2023/0060181 A1 Mar. 2, 2023

Related U.S. Application Data

(60) Provisional application No. 63/232,458, filed on Aug. 12, 2021.

(51) Int. Cl.

| | | |
|---|---|---|
| C08F 251/00 | (2006.01) |
| A61K 8/11 | (2006.01) |
| A61K 8/91 | (2006.01) |
| A61Q 5/02 | (2006.01) |
| A61Q 5/12 | (2006.01) |
| A61Q 19/10 | (2006.01) |
| B01J 13/16 | (2006.01) |
| C11D 3/00 | (2006.01) |
| C11D 3/37 | (2006.01) |
| C11D 3/50 | (2006.01) |

(52) U.S. Cl.
CPC .............. *C08F 251/00* (2013.01); *A61K 8/11* (2013.01); *A61K 8/91* (2013.01); *A61Q 5/02* (2013.01); *A61Q 5/12* (2013.01); *A61Q 19/10* (2013.01); *B01J 13/16* (2013.01); *C11D 3/001* (2013.01); *C11D 3/3788* (2013.01); *C11D 3/505* (2013.01); *A61K 2800/624* (2013.01); *A61K 2800/654* (2013.01); *C11D 2111/12* (2024.01)

(58) Field of Classification Search
CPC ........... C08F 251/00; A61K 8/11; A61K 8/91; A61K 2800/624; A61K 2800/654; A61Q 5/02; A61Q 5/12; A61Q 19/10; B01J 13/16; C11D 3/001; C11D 3/3788; C11D 3/505; C11D 2111/12
See application file for complete search history.

(56) References Cited

U.S. PATENT DOCUMENTS

| | | |
|---|---|---|
| 2,573,900 A | 11/1951 | Freeman |
| 3,345,358 A | 10/1967 | Inklaar |
| 3,819,838 A | 6/1974 | Smith et al. |
| 3,870,542 A | 3/1975 | Ida et al. |
| 4,076,774 A | 2/1978 | Short |
| 4,396,670 A | 8/1983 | Sinclair |
| 4,626,471 A | 12/1986 | Chao |
| 4,818,539 A | 4/1989 | Shaw et al. |
| 5,015,527 A | 5/1991 | Chao |
| 5,126,151 A | 6/1992 | Bodor et al. |
| 5,227,446 A | 7/1993 | Denzinger et al. |
| 5,550,189 A | 8/1996 | Qin et al. |
| 5,574,179 A | 11/1996 | Wahl et al. |
| 5,601,760 A | 2/1997 | Rosenberg |
| 5,837,747 A | 11/1998 | Soon-Shiong et al. |
| 6,248,909 B1 | 6/2001 | Akimoto et al. |
| 6,465,016 B2 | 10/2002 | Parikh et al. |
| 6,572,919 B2 | 6/2003 | Westland et al. |
| 6,596,073 B1 | 7/2003 | Nyssen et al. |
| 6,855,335 B2 | 2/2005 | Seok et al. |
| 7,431,986 B2 | 10/2008 | Van Lengerich et al. |
| 8,900,495 B2 | 12/2014 | Pacorel et al. |
| 8,993,041 B2 | 3/2015 | To et al. |
| 9,205,395 B2 | 12/2015 | Yan |
| 9,332,774 B2 | 5/2016 | Nakhasi et al. |
| 9,416,050 B2 | 8/2016 | Seidl et al. |

(Continued)

FOREIGN PATENT DOCUMENTS

| | | |
|---|---|---|
| CA | 1049335 A | 2/1979 |
| CN | 114539887 A | 5/2022 |

(Continued)

OTHER PUBLICATIONS

Jardine. (2022). Amino-functionalized polysaccharide derivatives: Synthesis, properties and application. Current Research in Green and Sustainable Chemistry 5, 100309.

Gasparini et al. (2020). Quantification of residual perfume by Py-GC-MS in fragrance encapsulate polymeric materials intended for biodegradation tests. Molecules, 25, 718.

Larson et al. (2017). Bulky polar additives that greatly reduce the viscosity of concentrated solutions of therapeutic monoclonal antibodies. Journal of Pharmaceutical Sciences, 106, 1211-1217.

(Continued)

*Primary Examiner* — Doan T Phan

(74) *Attorney, Agent, or Firm* — Caesar Rivise, PC

(57) ABSTRACT

Disclosed is a modified biopolymer having the formula A-XY wherein: (a) A is a starting material selected from the group consisting of a polysaccharide, a protein and a cellulose; (b) X is a first moiety bearing a functionality co-reactive with A; (c) Y is a second moiety covalently bound to X, capable of undergoing free radical polymerization and bearing at least two ethylenically unsaturated functional groups; (d) the starting material A and the first moiety X are linked covalently through linkages selected from the group consisting of an ester, an amide, a urethane, a urea, a sulfonate ester, a phosphate ester and an ether; and (e) a degree of substitution of the starting material A with the first moiety X is less than 0.5 but more than 0.1. Compositions including the modified biopolymer and methods for making them are also disclosed.

15 Claims, 1 Drawing Sheet

(56) References Cited

U.S. PATENT DOCUMENTS

| | | | |
|---|---|---|---|
| 9,427,719 | B2 | 8/2016 | Viaud-Massuard et al. |
| 9,714,397 | B2 | 7/2017 | Feng et al. |
| 9,937,477 | B2 | 4/2018 | Zhang et al. |
| 9,944,886 | B2 | 4/2018 | Hitchcock et al. |
| 9,993,401 | B2 | 6/2018 | Barnett et al. |
| 10,188,593 | B2 | 1/2019 | Dihora et al. |
| 11,179,302 | B2 | 11/2021 | Dardelle |
| 11,344,502 | B1 | 5/2022 | Dihora et al. |
| 11,465,117 | B2 | 10/2022 | Bachawala et al. |
| 11,484,857 | B2 | 11/2022 | Bachawala et al. |
| 11,542,392 | B1 | 1/2023 | Multari |
| 11,547,978 | B2 | 1/2023 | Bachawala et al. |
| 11,571,674 | B1 | 2/2023 | Dihora et al. |
| 2002/0169233 | A1 | 11/2002 | Schwantes |
| 2004/0017017 | A1 | 1/2004 | Van Lengerich et al. |
| 2004/0033264 | A1 | 2/2004 | Sawhney |
| 2005/0272628 | A1 | 12/2005 | Meli et al. |
| 2005/0276831 | A1 | 12/2005 | Dihora et al. |
| 2006/0069234 | A1* | 3/2006 | Kauffman ............ C08F 220/26 528/302 |
| 2007/0122455 | A1 | 5/2007 | Myers et al. |
| 2008/0085297 | A1 | 4/2008 | Dave et al. |
| 2008/0103265 | A1 | 5/2008 | Schocker et al. |
| 2008/0167188 | A1 | 7/2008 | Fischer et al. |
| 2009/0209661 | A1 | 8/2009 | Somerville Roberts et al. |
| 2010/0011610 | A1 | 1/2010 | Bittorf et al. |
| 2010/0028451 | A1 | 2/2010 | Kaplan et al. |
| 2011/0052680 | A1 | 3/2011 | Hendrickson et al. |
| 2011/0268778 | A1 | 11/2011 | Dihora et al. |
| 2011/0268802 | A1 | 11/2011 | Dihora et al. |
| 2012/0128752 | A1 | 5/2012 | Loo et al. |
| 2013/0004617 | A1 | 1/2013 | Zhang et al. |
| 2013/0022654 | A1 | 1/2013 | Deshmukh et al. |
| 2013/0084379 | A1 | 4/2013 | Gregson et al. |
| 2013/0239429 | A1 | 9/2013 | Vella et al. |
| 2014/0199244 | A1 | 7/2014 | Rijcken et al. |
| 2014/0335032 | A1 | 11/2014 | Panandiker et al. |
| 2015/0079139 | A1 | 3/2015 | Takehana |
| 2015/0252312 | A1 | 9/2015 | De Villeneuve et al. |
| 2016/0038428 | A1 | 2/2016 | Harel et al. |
| 2016/0128944 | A1 | 5/2016 | Chawrai et al. |
| 2016/0158121 | A1 | 6/2016 | Lei et al. |
| 2016/0166480 | A1 | 6/2016 | Lei et al. |
| 2016/0206561 | A1 | 7/2016 | Kohane et al. |
| 2016/0228338 | A9 | 8/2016 | Dihora et al. |
| 2017/0165627 | A1 | 6/2017 | Duan et al. |
| 2017/0360676 | A1* | 12/2017 | Dihora ................. C11D 3/3723 |
| 2018/0015009 | A1 | 1/2018 | Soubiran et al. |
| 2018/0042825 | A1 | 2/2018 | Lei et al. |
| 2019/0192444 | A1 | 6/2019 | Barzilay et al. |
| 2019/0275490 | A1 | 9/2019 | Bachawala |
| 2021/0045409 | A1 | 2/2021 | Witteveen et al. |
| 2022/0133603 | A1 | 5/2022 | Bachawala et al. |
| 2022/0177815 | A1* | 6/2022 | Popplewell ............ A01N 65/00 |
| 2022/0408771 | A1 | 12/2022 | Dihora |

FOREIGN PATENT DOCUMENTS

| | | |
|---|---|---|
| EP | 0076515 A1 | 4/1983 |
| EP | 0361677 B2 | 11/1993 |
| EP | 0815743 A2 | 1/1998 |
| EP | 1371410 A1 | 12/2003 |
| EP | 1797946 A2 | 6/2007 |
| RU | 2351364 C2 | 4/2009 |
| WO | 9901214 A1 | 1/1999 |
| WO | 0105926 A1 | 1/2001 |
| WO | 03013538 A1 | 2/2003 |
| WO | 2004064971 A2 | 8/2004 |
| WO | 2006024411 A2 | 3/2006 |
| WO | 2007135583 A2 | 11/2007 |
| WO | 2008118133 A2 | 10/2008 |
| WO | 2009098226 A1 | 8/2009 |
| WO | 2011041395 A2 | 4/2011 |
| WO | 2015091877 A1 | 6/2015 |
| WO | 2016071151 A1 | 5/2016 |
| WO | 2017023830 A1 | 2/2017 |
| WO | WO-2020092568 A2 * | 5/2020 ............ A61L 15/24 |
| WO | 2020195132 A1 | 10/2020 |

OTHER PUBLICATIONS

Guo et al. (2012). Structure-activity relationship for hydrophobic salts as viscosity-lowering excipients for concentrated solutions of monoclonal antibodies. Pharm Res, 3102-3109.

Kumar et al. (2017). Viscosity-reducing bulky-salt excipients prevent gelation of protein, but not carbohydrate, solutions. Appl Biochem Biotechnol, 1491-1496.

Wang et al. (2021). Hofmeister effect on the viscosity properties of gelatin in dilute solutions. Colloids and Surfaces B: Biointerfaces, 206, 111944.

OECD 301D method (OECD 1992, Test No. 301 Ready Biodegradability, OECD Guidelines for the Testing of Chemicals, Section 3, OECD Publishing, Paris, https://doi.org/10.1787/9789264070349-en.

Thakore et al. (2001). "Studies on biodegradability, morphology and thermo-mechanical properties of LDPE/modified starch blends." European polymer journal, 37(1), 151-160.

Adhesives Magazine (2016). Sartomer: Acrylate Oliogmer. Available at: https://www.adhesivesmag.com/articles/94922-sartomer-acrylate-oligomer.

Leung et al. (2017). Enteric coating of micron-size drug particles through a Wurster fluid-bed process. Powder Technology, 317, 247-252.

Luo et al. (2014). Zein-based micro-and nano-particles for drug and nutrient delivery: A review. Journal of Applied Polymer Science, 131(16): 40696, 1-12.

Silverajah et al. (2012). Mechanical, thermal and morphological properties of poly (lactic acid)/epoxidized palm olein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

English language abstract for WO 2020195132 A1 (2020).

http://polymerdatabase.com/polymer%20physics/sigma.html downloaded on Apr. 29, 2022.

Ko et al., "Characterization of hydrophilic-hydrophobic polymeric surfaces by contact angle measurements", Journal of Colloid and Interface Science, vol. 82(1) (1981).

* cited by examiner

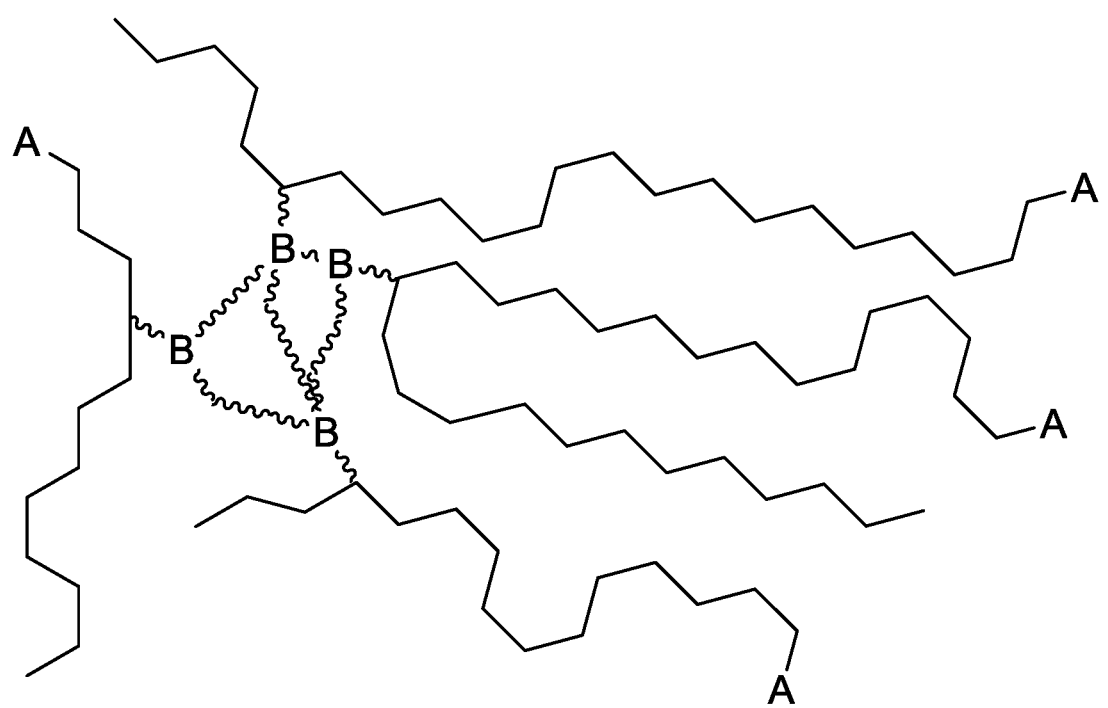

ENVIRONMENTALLY BIODEGRADABLE MICROCAPSULES

CROSS-REFERENCE TO RELATED APPLICATIONS

This application claims the benefit under 35 U.S.C. § 119(e) of U.S. Provisional Patent App. No. 63/232,458, filed Aug. 12, 2021, the contents of which application are incorporated herein by reference in their entireties for all purposes.

BACKGROUND OF THE INVENTION

1. Field of Invention

This invention relates to controlled release compositions, encapsulation compositions and methods for making and using them.

2. Description of Related Art

There are many microencapsulated delivery systems disclosed in the art to control the release of the encapsulated active, or provide release when a specific trigger is applied. Controlled release microcapsules that provide release of active upon application of shear force or friction generally suffer from several drawbacks: (1) such microcapsules are made of highly crosslinked membranes and membrane materials that cannot be broken down by microbes found in the environment, (2) despite such highly crosslinked membranes, the materials of construction of the membrane impart high permeabilities when incorporated into products that contain high levels of surfactant, solvents, and/or water, which results in the premature benefit agent release, (3) they can only effectively encapsulate a limited breadth of benefit agents, (4) they either are so stable that they do not release the benefit agent in use or have insufficient mechanical stability to withstand the processes required to incorporate them in and/or make a consumer product, (5) they do not adequately deposit on the surface that is being treated with consumer product that contains microcapsules, and/or (6) they do not comprise membrane materials that have a favorable environmental degradability profile.

Such microcapsules are made via chemical processes that require the development of a membrane at the oil-water interface. Said membrane can be developed from the oil side or the water side, or both. An emulsion comprising the active material (dispersed phase) is stabilized in a continuous phase. In one mode, a shell material is deposited from the continuous phase onto a dispersed phase via precipitation of the shell material. In another mode, the shell material is manufactured within the dispersed phase, and migration of the shell material is induced via an interfacial reaction or insolubility of the shell material in the oil phase. The two approaches could be combined to develop "multi-shell" capsules.

There is a challenge in designing a membrane that minimizes the diffusion of the encapsulated active into the surrounding formulation, and yet is environmentally biodegradable. Environmentally biodegradable polymers generally swell in water or are soluble in water. In contrast, microcapsule membranes generally need to resist swelling or dissolution in aqueous cleaning product formulation. A high degree of crosslinking within the membrane can reduce swelling and solubility; however, such highly crosslinked membranes are difficult for environmentally available microbes to digest and breakdown.

A study on biodegradability of LDPE/starch blend by Thakore et al. [European Polymer Journal 37 (2001) 151-160] shows that for a physical mixture comprising 20 wt. % of a natural material having 100% environmental biodegradability combined with 80 wt. % of a material having 0% biodegradability, wherein there is no chemical reaction taking place between the components, one would expect that the final material would have 20% biodegradability. However, the results explicitly point out that the biodegradability is reduced to 10%. The biodegradability of a membrane is not only dependent on the components that make up the membrane, but how these components are interacting with one another (reaction vs. physical mixture), and the accessibility of the materials to the microbes that will digest these materials.

In WO2020195132A1, Fujifilm clarifies that when isocyanates dissolved in the core material are reacted with highly biodegradable resins in the water phase (e.g. gelatin, chitosan, celluloses), the resulting interfacial membrane shows an increase in biodegradability; however, it is nowhere close to the biodegradability of the biodegradable resin. The inventors also show that an increase in crosslink density is necessary to minimize the diffusion of the core material through the membrane. Such increase in crosslink density reduces the environmental biodegradability of the membrane.

While others have attempted to improve the barrier properties of microcapsules, there remains significant shortcomings and limitations in the art. For example, U.S. Pat. No. 9,944,886B2 to Hitchcock et al. describes metal coated microcapsules with improved barrier properties. The Hitchcock metal coating is developed after the formation of the microcapsule membrane, via the use of sterically stabilized nanosuspension of metal particle. Such metal coated microcapsules could improve barrier properties; however, it is difficult to imagine how the encapsulated active would be released, since a metal coating would be difficult to fracture. Furthermore, the processing steps involved to achieve the metal coating are laborious and expensive. Moreover, such metal coating could render the microcapsules non-environmentally biodegradable.

US2011/0268778A1 (Dihora et al.) provides microcapsules made using UV initiation in order to form membranes at lower temperatures. However, prior to the free radical polymerization to form the membrane, the hydrophobic active material needs to be heated to temperatures beyond 60° C. Moreover, Example 2 of the application clearly delineates poorer barrier properties of the membrane made via UV initiator versus the same capsules made via use of thermal initiation. Because of the non-transparency of the system, UV initiation to form a membrane has low efficiency. The resulting barrier properties and biodegradability of the resulting polyacrylate microcapsules are poor.

U.S. Pat. No. 9,937,477B2 (Zhang et al.) discloses core/shell microcapsules that are manufactured using free radical polymerization of acrylates. Such microcapsules require multi-step reactions that require heating the capsules to 95° C. for up to 6 hours. It is well known that such polyacrylate capsules that are highly crosslinked have poor environmental biodegradability.

U.S. Pat. No. 5,837,747 (Soon-Shiong et al.) teaches human physiologically compatible materials capable of undergoing light induced free radical polymerization. The inventors describe methods to modify synthetic and natural materials to make microcapsules containing biologically active materials. Such modified materials are crosslinked in the aqueous phase to yield gels, and the crosslink density can be manipulated to control the release rate of the biological active. A higher crosslink density requires a higher degree of substitution of the free radical polymerizable components onto the natural materials. This higher degree of substitution significantly reduces the biodegradability of the natural material. A high degree of crosslinking is necessary to achieve low permeability of the encapsulated active, especially when the controlled release particle comprising the active are incorporated into an aqueous formulated product containing surfactants, polymers, and solvents.

Conventional controlled release particles that comprise a core and a shell have several limitations. First, such capsules prematurely release the active material when suspended in a finished product formulations, such as cleaning product formulations. Second, such capsules have poor environmental biodegradability due to the nature of materials used and the degree of crosslinking that is achieved in order to reduce the diffusion of the active. Third, it is difficult to control the release profile of the encapsulated active. Fourth, poor adhesion of particles to the substrate result in significant loss of the particles, especially when formulations containing such particles are used in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water.

It is therefore desired to provide a modified biomaterial suitable for producing controlled release particles, wherein the modified biomaterial can achieve a high crosslink density while maintaining an Environmental Biodegradability Index greater than 50.

It is further desired to provide a method to manufacture controlled release particles comprising said modified biomaterial.

It is still further desired to provide microcapsules that are processed at temperatures at or below 95° C., with a batch cycle time of less than 24 hours, wherein the microcapsules have a degree of crosslinking sufficient to reduce the diffusion of the encapsulated active out of the microcapsule yet provide a membrane material having an Environmental Biodegradability Index of more than 50.

It is still further desired to provide low permeability microcapsules that retain the encapsulated active in surfactant containing solutions, or under highly dilute aqueous conditions.

It is still further desired to improve the adhesion of microcapsules onto the desired substrate during rinse-off applications.

It is still further desired to release the encapsulated active in larger quantities, and over a longer duration of time.

It is still further desired to have capsules that have a favorable environmental biodegradability profile as defined by OECD 301D method (OECD 1992, Test No. 301 Ready Biodegradability, OECD Guidelines for the Testing of Chemicals, Section 3, OECD Publishing, Paris, https://doi.org/10.1787/9789264070349-en).

All references cited herein are incorporated herein by reference in their entireties. The citation of any reference is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

Accordingly, a first aspect of the invention relates to a modified biopolymer having the formula A-XY wherein:
  A is a starting material selected from the group consisting of a polysaccharide, a protein and a cellulose;
  X is a first moiety bearing a functionality co-reactive with the starting material A;
  Y is a second moiety covalently bound to the first moiety X, capable of undergoing free radical polymerization and bearing at least two ethylenically unsaturated functional groups;
  the starting material A and the first moiety X are linked covalently through linkages selected from the group consisting of an ester, an amide, a urethane, a urea, a sulfonate ester, a phosphate ester and an ether; and
  a degree of substitution of the starting material A with the first moiety X is less than 0.5 but more than 0.1.

In certain embodiments, the starting material A is a polysaccharide selected from the group consisting of tapioca, potato, corn, rice, wheat, carboxymethyl starch, carboxymethyl chitosan, chitosan oligosaccharide, and octenyl succinic anhydride modified starch.

In certain embodiments, the starting material A is a protein selected from the group consisting of casein, whey protein, soy protein, fish protein, gelatin, silk fibroin, sunflower protein, modified natural proteins and non-naturally occurring polypeptides.

In certain embodiments, the starting material A is a cellulose selected from the group consisting of carboxy modified cellulose, hemicellulose and oxidized cellulose.

In certain embodiments, the starting material A is a polysaccharide, protein or cellulose that is adjusted to a lower molecular weight before incorporation into the modified biopolymer.

In certain embodiments, the first moiety X is t-butyl acetoacetate or t-butyl cyanoacetate.

In certain embodiments, the first moiety X is a Michael adduct of alkyl acetoacetate or alkyl cyanoacetate with ethylenically unsaturated monomer bearing an anhydride functionality, an epoxy functionality, an isocyanate functionality or an oxazoline functionality.

In certain embodiments, the second moiety Y comprises at least three ethylenically unsaturated groups.

A second aspect of the invention relates to a composition comprising controlled release particles, wherein each of the controlled release particles comprises: at least one hydrophobic active ingredient; and a reaction product of at least one modified biopolymer of the invention and at least one ethylenically unsaturated monomer.

In certain embodiments, the composition further comprises at least one of a free radical initiator, a cationic deposition aid, an isocyanate, an epoxy, an organofunctional silane, an epoxide curing agent, a plasticizer and an inorganic solid particle.

In certain embodiments, the at least one hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the controlled release particles have a diameter from 0.1 microns to less than 200 microns.

In certain embodiments, the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

In certain embodiments, the composition comprises two different controlled release particles which are friction-triggered release microcapsules which release the at least one hydrophobic active ingredient at different rates due to a difference in shell material friability or core material viscosity.

In certain embodiments, the at least one hydrophobic active ingredient comprises a mixture of a hydrophobic active and a material selected from the group consisting of brominated oils, epoxidized oils, highly nonpolar oils, dispersible organic particles, dispersible inorganic particles, nonionic emulsifiers and oil thickening agents.

In certain embodiments, a wall material of the controlled release particles has an Environmental Biodegradability greater than 30%.

A third aspect of the invention relates to a method of preparing a composition comprising controlled release particles, said method comprising the sequential steps of:
 (a) preparing an oil phase, wherein the oil phase comprises:
  (i) at least one hydrophobic active ingredient, and at least one ethylenically unsaturated monomer or free radical initiator; or
  (ii) at least one hydrophobic active ingredient, at least one ethylenically unsaturated monomer and free radical initiator and optionally one or more of the following compounds: an isocyanate, an epoxy, an organofunctional silane, an epoxide curing agent, a plasticizer and an inorganic solid particle;
 (b) preparing an aqueous phase comprising a modified biopolymer, and optionally an emulsifier, buffer, ionic strength modifier or water soluble free radical initiator;
 (c) combining the oil phase and the aqueous phase to emulsify the at least one hydrophobic active ingredient to provide an aqueous suspension of the at least one hydrophobic active ingredient;
 (d) heating the aqueous suspension; and
 (e) adding structuring agents to the aqueous suspension to provide the controlled release particles homogeneously suspended in an aqueous dispersion.

In certain embodiments of the method, the free radical initiator is a member selected from the group consisting of azo initiators and alkyl peroxides.

In certain embodiments of the method, the at least one suspension agent is included in the composition to suspend the controlled release particles, wherein the at least one suspension agent is at least one member selected from the group consisting of a rheology modifier, a structurant and a thickener.

In certain embodiments of the method, the at least one suspension agent has a high shear viscosity at, 20 sec$^{-1}$ shear rate and at 21° C., of from 1 to 7000 cps and a low shear viscosity, at 0.5 sec$^{-1}$ shear rate at 21° C., of greater than 1000 cps.

In certain embodiments of the method, a finished capsule slurry is a fluid having a high shear viscosity, at 20 sec$^{-1}$ and at 21° C., of from 50 to 3000 cps and a low shear viscosity, at 0.5 sec$^{-1}$ shear rate at 21° C., of greater than 1000 cps.

In certain embodiments of the method, the at least one suspension agent is a member selected from the group consisting of polyacrylates, polymethacrylates, polycarboxylates, pectin, alginate, gum arabic, gelatin, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax, perfume oil, and mixtures thereof.

A fourth aspect of the invention relates to a composition comprising controlled release particles prepared by the method of the invention.

BRIEF DESCRIPTION OF THE DRAWING

The invention will be described in conjunction with the following drawing, wherein FIG. 1 shows a theoretical representation of an embodiment of a modified biopolymer of the invention, comprising a natural biopolymer (A) and functional groups (B) that modify the natural biopolymer.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell," "membrane" and "wall" are synonyms, which refer to barriers at least partially surrounding the core of the particles of the invention.

As used herein, microcapsules "formed under acidic conditions" means that part of the process of forming the microcapsule involves a step where the pH of the suspension in which the microcapsules form is adjusted into the acidic region (less than 7).

As used herein, microcapsules "formed under basic conditions" means that part of the process of forming the microcapsule involves a step where the pH of the suspension in which the microcapsules form is adjusted into the alkaline region (greater than 7).

As used herein, "an unreacted amount" refers to the amount of a reactant not used up in one or more reaction. "An unreacted amount" can be zero to any amount depending on the amount of reactants added.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multifunctional absorbent and cleaning uses (absorbent towels such as paper towel products and/or wipe products). The sanitary tissue products of the invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to 2% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Advantages of the Invention

We have discovered that the modification of natural materials with reactive functional groups needs to be done in such a way that minimally disturbs the natural material. For example, U.S. Pat. No. 5,837,747 talks about a modified biocompatible material having the formula A-X where A is a natural material and X is a moiety capable of undergoing free radical polymerization. To achieve a high crosslink density, the degree of substitution of A by X must be high. We have found that the degree of substitution of natural materials is critical to maintain Environmental Biodegradability of the natural material.

Table 1 shows the environmental biodegradability of various modified natural materials. The control sample is simply maltodextrin with dextrose equivalent of 18. The modified control is maltodextrin that has been pH adjusted with sodium hydroxide, to reflect the effect of imposing reaction conditions that were used during the modification of the maltodextrin material in the subsequent polymer samples. Polymer 1 and Polymer 2 have a very high degree of substitution, and clearly show a significant reduction in environmental biodegradability. Polymers 3, 4, and 5 have much lower degree of substitution, and clearly show that such modified biopolymers maintain an environmental biodegradability greater than 30%.

TABLE 1

OECD 301D Closed Bottle Test of Modified Biomaterials

| Lot info | Polymer Info | COD (mg $O_2$/mg solids) | % Degradation | | | |
|---|---|---|---|---|---|---|
| | | | 7 days | 14 days | 21 days | 28 days |
| Reference | Sodium Benzoate Control | 1.67 | 97% | 100% | | |
| Control | Maltrin Ml 80 Powder | | 59% | 63% | 86% | 84% |
| Modified Control | Maltodextrin with NaOH for 4 h then pH adjusted to 7.4 | 1.20 | 51% | 62% | 70% | 63% |
| Polymer 1 | Propylene diamine modified Maltrin M180, DS = 0.80; 5.5 mmol/g | | 3% | 4% | 7% | 8% |
| Polymer 2 | Propylene diamine modified Maltrin M180 + Monoepoxy DS = 0.80; 5.5 mmol/g | | 1% | 2% | 0.9% | 3% |
| Polymer 3 | Maltodextrin M040 ethylamine, pH 7.4, DS = 0.24; 1.96 mmol/g | 1.13 | 37% | 49% | 64% | 62% |
| Polymer 4 | Maltodextrin M040 Propylamine, DS = 0.1; 2.6 mmol/g | 1.23 | 22% | 27% | 33% | 62% |
| Polymer 5 | 23.6% Solids, acetoacetated dextran | 1.06 | 40% | 55% | 49% | 60% |

Such modified biomaterials can be used to make controlled release particles. Modified biomaterials with a low degree of substitution yields microcapsules with high permeability, a high degree of swelling, and high leakage when capsules are incorporated into a liquid formulated product containing surfactants. Microcapsules made with a high degree of substitution yield microcapsules with lower permeability, a low degree of swelling, and lower leakage of the encapsulated active material when incorporated into a liquid formulated product containing surfactants. However, such microcapsule membranes have an Environmental Biodegradability less than 30%.

The invention relates to microcapsules comprising a core and shell, wherein the shell comprises a membrane developed around the core material to reduce the diffusion of core material into the environment. The inventors have surprisingly found that biodegradable microcapsules having good mechanical and chemical properties and composed mainly of natural products can be prepared by decoupling shell crosslink density and degree of substitution of the natural product. The invention is aimed at increasing the links between neighboring natural product polymers without increasing the points of attachment on any one natural product backbone. Said differently, the invention achieves a modified biopolymer with a low degree of substitution, but that substitution is done in a novel way to achieve dendritic links between the natural product polymers to achieve a high crosslink density.

FIG. 1 shows a theoretical representation of an embodiment of a modified biopolymer after polymerization showing the higher crosslink density potentially achievable with the inventive modified biopolymer. In FIG. 1, A represents a biopolymer chain and B represents the multifunctional acrylate which, when polymerized, can achieve locally high crosslink densities.

The prior art (for example, U.S. Pat. No. 5,837,747) generally discloses natural polymers with pendant modifications B at degrees of substitution greater than 0.5. Such modified natural materials have a number of deficiencies: 1) the higher degree of substitution significantly reduces the natural material's environmental biodegradability (see Table 1), 2) a lower local crosslink density results since only one crosslink is possible at each pendant group, and 3) the overall crosslink density is reduced due to steric hindrance and inflexibility of polymers as the polymer molecular weight grows. The novel polymer design of the instant invention preserves the environmental biodegradability properties of the natural polymer whilst achieving sufficient crosslinking density.

In particular, at least one of the following benefits are provided by preferred embodiments of the invention.

The shell material of the inventive particles has an environmental biodegradability greater than 30% as measured by the OECD 301D method that utilizes biological oxygen demand as the criteria for measuring degradability. Conventional capsules utilize polymers that may be biodegradable prior to shell formation, but due to the nature of crosslinkers that are used and the chemical structure of the final crosslinked polymer, microbes are no longer able to attach to the polymer or the backbone to sufficiently degrade the shell material. The inventive particles utilize monomers and polymers that retain degradable functional groups even after the crosslinking is complete, such that microbes in the environment are able to digest the shell material.

The inventive particles adhere onto desired substrates via the use of viscoelastic and electrostatic interactions. By adhering large particles as well as small particles during the rinse off application, greater volumes of active material can be delivered with a higher delivery efficiency of the encapsulated active. Conventional capsules are limited to the deposition of small particles, which carry much less volume of active material. Only a fraction of these small microcapsules fracture during use, resulting in significantly lower delivery efficiency of the encapsulated active. Moreover, inventors have discovered formulation approaches to control the level of aggregation of capsules such that a higher quantity of microcapsules can be retained onto the substrate during a rinse-off or filtration process. Such discovery can reduce the quantity of capsules that are lost in the rinse water, and can reduce the environmental impact.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active. Improvement of retention of capsules onto the fabric during rinse-off processes also has the potential to reduce cost.

Modified Biopolymer

Biopolymers are modified in accordance with the invention for enhanced radical reactivity. In certain embodiments, the biopolymer is degraded enzymatically, with strong acid or base or with oxidants to reduce molecular weight prior to modification for enhanced radical reactivity. A reactive intermediate, XY, is preferably used to modify the biopolymer to form the modified biopolymer with enhanced free radical reactivity.

Thus, a first aspect of the invention relates to a modified biopolymer having the formula A-XY wherein:

A is a starting material selected from the group consisting of a polysaccharide, a protein and a cellulose;

X is a first moiety bearing a functionality co-reactive with the starting material A;

Y is a second moiety covalently bound to the first moiety X, capable of undergoing free radical polymerization and bearing at least two ethylenically unsaturated functional groups;

the starting material A and the first moiety X are linked covalently through linkages selected from the group consisting of an ester, an amide, a urethane, a urea, a sulfonate ester, a phosphate ester and an ether; and a degree of substitution of the starting material A with the first moiety X is less than 0.5 but more than 0.1.

In certain embodiments, the modified biopolymer component A is a polysaccharide selected from the group consisting of natural starches such as tapioca, potato, corn, rice, wheat; modified starches such as carboxy modified polysaccharide or cellulose such as carboxymethyl starch, carboxymethyl chitosan, chitosan oligosaccharide, and octenyl succinic anhydride modified starch.

In certain embodiments, the biopolymer A is a protein selected from the group consisting of natural proteins such as casein, whey protein, soy protein, fish protein, sunflower protein, and modified or non-natural polypeptides. Commercially available examples of proteins comprise unmodified silk protein, zein, gelatin, keratin, collagen and any polypeptide, such as polylysine; hydrolyzed proteins such as COLLASOL (high molecular weight, soluble, marine collagen; Croda), CROPEPTIDE (hydrolyzed wheat protein and hydrolyzed wheat starch; Croda), CROSILK 10000 (hydrolyzed silk protein; Croda), CROTEIN (hydrolyzed collagen; Croda), HYDROLACTIN 2500 (hydrolyzed milk protein; Croda), HYDROSOLANUM (hydrolyzed vegetable protein; Croda), HYDROSOY 2000 PE (hydrolyzed soy protein; Croda), HYDROTRITICUM 2000 PE (hydrolyzed wheat protein; Croda), KERASOL (hydrolyzed keratin; Croda), PROLEVIUM (cottonseed protein hydrolyzate; Croda), PROSINA (hydrolyzed keratin; Croda), TRITISOL (Hydrolyzed wheat protein; Croda), Fision KeraVeg 18 (wheat amino acids, soy amino acids; Tri-K), MILK-TEIN (hydrolyzed milk protein; Tri-K), Rice PRO-TEIN (hydrolyzed rice protein; Tri-K), RICE-QUAT C (cocodimonium hydroxypropyl hydrolyzed rice protein; Tri-K), SOY-QUAT L (laurdimonium hydroxypropyl hydrolyzed soy protein; Tri-K), WHEAT-QUAT C (cocodimonium hydroxypropyl hydrolyzed wheat protein; Tri-K), QUINOA PRO EX (hydrolyzed quinoa; Tri-K), BARLA-TEIN Pro (hydrolyzed barley protein; Tri-K), KERA-QUAT WKP (hydrolyzed keratin; Tri-K), KERA-TEIN 1000 (hydrolyzed keratin; Tri-K), KERA-TEIN 1000 SD (hydrolyzed keratin; Tri-K), Proto-lan 8 (cocoyl hydrolyzed collagen; Tri-K), Proto-lan KT (cocoyl hydrolyzed collagen; Tri-K), SILK AA-QUAT C (cocodimonium hydroxypropyl silk amino acids; Tri-K), AMINO SILK SF (silk amino acids; Tri-K), Collagen Hydrolyzate Cosmetic N-55 (Tri-K), FLAX-TEIN Pro (hydrolyzed linseed protein; Tri-K), SOY-TEIN NL (hydrolyzed soy protein; Tri-K), Silk PRO-TEIN (hydrolyzed silk; Tri-K), WHEAT-TEIN W (hydrolyzed wheat protein; Tri-K), and MARI-COLL N-30 (hydrolyzed collagen; Tri-K).

The modified biopolymer component A can comprise carboxy modified polysaccharides or celluloses such as carboxymethyl starch, carboxy methyl cellulose, oxidized starch, oxidized cellulose, carboxymethyl chitosan, chitosan oligosaccharide, hydroxypropyl methyl starch, hydroxypropyl cellulose, ethyl cellulose, methyl cellulose, and octenyl succinic anhydride modified starch. In addition, the biopolymer may be modified by covalent attachment of natural or synthetic polymer (for example, through grafting as disclosed in U.S. Pat. No. 5,227,446)

The component X is chosen such that it bears two reactive groups, one reactive with biopolymer A and the other reactive with Y. The two reactive groups on X are preferably different from each other and do not react with each other. The biopolymer co-reactive group on X is at least one member of the group consisting of anhydrides, ketenes, isocyanates, oxazolines, epoxies, and halides. Also included are precursors of the above which form the desired functionality in-situ (e.g. chlorohydrins, blocked isocyanates, ketene generating precursors, etc.).

The (meth)acrylate reactive group on X is at least one member of the group consisting of acetoacetate, cyanoacetate, thiol and alkoxide. Also included are precursors of the above which form the desired functionality in-situ (e.g. thiolactone, xanthate, etc.). Preferably, the (meth)acrylate functional reactive group on X is an acetoacetate, a cyanoacetate or a reaction product of an acetoacetate or cyanoacetate with ethylenically unsaturated monomer bearing a biopolymer reactive functionality.

The reactive component, Y, is covalently attached to X and contains free radical polymerizable functionality. In certain embodiments, the reactive component Y is at least one member selected from the group consisting of free radical polymerizable monomers where the number of ethylenically unsaturated groups is 3 or more. Reactive component Y is chosen such that, after attachment to X, there remain at least 2 ethylenically unsaturated groups in the final XY modifier. Examples of Y include trimethylolpropane triacrylate, pentaerythritol triacrylate, penterythritol tetraacrylate, dipentaerythritol pentaacrylate, tris-2-hydroxethyl isocyanurate triacrylate, urethane polyacrylates such as CN 9026 (Sartomer) and CN9010 (Sartomer), ethoxylated and propoxylated TMPTA such as Miramer M3130 (Miwon), Miramer M3160 (Miwon), Miramer M360 (Miwon) and their methacrylate versions.

In certain embodiments, the ethylenically unsaturated monomer is an acrylate, methacrylate, styrenic, vinyl ester or vinyl ether bearing one or more ethylenically unsaturated groups and optionally containing functionality to improve compatibility with modified biopolymer (e.g. hydroxyl, ether, carboxylic, amino, strong acid or strong acid ester).

It is preferable to attach X and Y via Michael addition. The reaction can be performed neat or in solvent and is catalyzed by strong base. Typically, the reaction will occur at room temperature but can be heated, as necessary, to speed the overall reaction. The reaction temperature, the duration of the reaction and the base strength can impact the structure of the final Michael adduct. In the case of polyfunctional acrylates, over reaction or oligomerization can be avoided with proper choice of base and processing conditions. Generally preferred are intermediate to strong bases that range in pKa from ~8 to ~14. Examples of such bases are n-ethyl piperidine, 1,8-diazobicyclo[5.4.0]undec-7-ene (DBU), tetraethylammonium hydroxide, tetrabuylammonium hydroxide, sodium methoxide, potassium carbonate, potassium acetate, potassium octoate, tetrabutylammonium acetate.

Particles

The invention addresses one or more of the prior art deficiencies described above by providing controlled release particles. The particles are particularly well-suited for use in encapsulation of hydrophobic, nonpolar materials.

Thus, a second aspect of the invention relates to a composition comprising controlled release particles, wherein each of the controlled release particles comprises: at least one hydrophobic active ingredient; and a reaction product of at least one modified biopolymer of the invention and at least one ethylenically unsaturated monomer.

The particles are preferably used in a consumer product composition, such as, e.g., a cleaning composition, a fabric care composition and/or a personal care composition.

The particles preferably comprise a hydrophobic active ingredient surrounded by a wall material. Such wall material is comprised mainly of biopolymer or modified biopolymer in the form of A-XY, as defined earlier.

The biopolymers are present in particles of the invention in an amount effective to enhance the environmental biodegradability of the particles. The amount of biopolymer on a dry basis (weight of biopolymer per weight of dry matter in the suspension) can be, e.g., from 50 wt. % or 55 wt. % or 60 wt. % or 65 wt. % to 70 wt. % or 75 wt. % or 80 wt. %.

The modified biopolymer may be delivered in several ways to form the capsules of the invention. Preferably, the modified biopolymer is water soluble or water dispersible. Modified biopolymer may also be dispersed in hydrophobic active as an organic solid.

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 47 wt. % or 59 wt. % or 66 wt. % to 73 wt. % or 78 wt. % or 81 wt. % or 93.5 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a pheromone, phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, neobee, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylamino-phenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Suitable moldicides further include but are not limited to fungicidal compounds such as, e.g., isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethyl-isothiazolinone, 4,5-Dichloro-2-n-octyl-3 (2H)-isothiazolone and 1,2-benzisothiazolin one.

Suitable herbicides include but are not limited to 2-(2-chloro methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point.

Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying agents include unsaturated natural resins such as rosin or derivatives thereof, such as rosin esters of polyols such as glycerol or pentaerythritol, hydrogenated rosins or dehydrogenated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

Suitable free radical initiators are selected from the classes of azo initiators and peroxides (peroxyesters, percarbonates, hydroperoxides and persulfates). Examples of free radical initiators are Vazo 52 and Vazo 67, Vazo 56, Vazo 68 (Chemours Inc), t-butyl perpivalate, t-butyl peroctoate, Perkadox 16 (Nouryon), cumyl peroxyneodecanoate, t-butyl hydroperoxide, ammonium persulfate, In certain embodiments, the free radical initiator is thermally decomposed to form radicals or is coupled with additional coreactants to form a redox couple. Examples of such redox systems are peroxyesters with tertiary aromatic arrive or peroxides with metal salts and antioxidant agents such as phosphites, mercaptans, aldehydes and ketone and their bisulfite reaction products, polysaccharides, erythorbic acid and the like.

The ethylenically unsaturated monomer is preferably a member selected from the group consisting of mono and di-functional acrylates and methacrylates.

The application of high shear is often necessary to form the desired droplet size for capsules of the invention. Often this can be achieved by mixer, homogenizer or sonication. Application of high shear may be intermittent or continuous. Preferably, shear is applied once or intermittently as needed to maintain particle size.

The formed droplets may be further stabilized with emulsifiers. The emulsifier is present in the suspension, on a dry basis (weight of emulsifier per weight of dry matter in the suspension), of the invention in an amount effective to achieve the desired particle size distribution. The amount can be, e.g., from about 1.5 wt. % to about 10 wt. % or at least 1.5 wt. %, or at least 5 wt. % or at least 7.4 wt. % or at least 8.2 wt. %, or at least 10 wt. % or not greater than 20 wt. %.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17. Of course, emulsifiers/surfactants of lower and higher HLB values that achieve the same objective as noted are also included.

Exemplary emulsifiers include, but are not limited to gums such as acacia gum, gum arabic, konjac gum, and xantham gum; poly(meth)acrylic acids and derivatives. Most preferably, the emulsifier/emulsion stabilizer is a polyvinyl pyrrolidone, copolymers of polyvinyl pyrrolidone with vinyl acetate, vinyl alcohol, vinyl imidazole; polyglycerol oleates.

In certain embodiments, the emulsifier is a member selected from the group consisting of polyalkylene glycol ether; polyvinyl acetate; copolymers of polyvinyl acetate; polyacrylamide; poly(N-isopropylacrylamide); poly (2-hydroxypropyl methacrylate); poly(2-ethyl-2-oxazoline); poly (2-isopropenyl-2-oxazoline-co-methyl methacrylate); poly (methyl vinyl ether); polyvinyl alcohol-co-ethylene; polyvinyl pyrrolidone; copolymers of polyvinyl pyrrolidone; 1H-Imidazolium, 1-ethenyl-3-methyl-, chloride; polymer with 1-ethenyl-2-pyrrolidinone; vinyl acetate; Hydroxypropyl methyl cellulose; gum arabic; palmitamidopropyltrimonium chloride; distearyl dimonium chloride; cetyltrimethylammonium chloride; quaternary ammonium compounds; fatty amines; aliphatic ammonium halides; alkyldimethyl benzylammonium halides; alkyldimethylethylammonium halides; polyethyleneimine; poly(2-dimethylamino)ethyl methacrylate)methyl chloride quaternary salt; poly(1-vinylpyrrolidone-co-2-dimethylaminoethyl methacrylate); poly(acrylamide-co-diallyldimethylammonium chloride); poly(allylamine); polybis(2-chloroethyl)ether-alt-1,3-bis(3-(dimethylamino) propylurea quaternized; and poly(dimethylamine-co-epichlorohydrin-co-ethylenediamine.

Additional exemplary anionic surfactants and classes of anionic surfactants suitable for use in the practice of the invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelalkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkylphosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, 1H-Imidazolium, 1-ethenyl-3-methyl-, chloride, polymer with 1-ethenyl-2-pyrrolidinone, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; sorbitol ester alkoxylates; ethoxylated castor oil; amides of fatty acids such as stearamide, lauramide diethanolamide, and lauramide monoethanolamide; aryl ethers of polyoxyalkylene glycols such as polyoxyethylene glycol nonylphenyl ether and polypropylene glycol stearyl ether. Also preferred as non-ionic emulsifiers are various latex materials, stearates, lecithins, In certain embodiments, additional pre-reacted natural material comprising the reaction product of a biopolymer and crosslinker may be included in the inventive capsules. The natural material is selected from the group consisting of protein, polysaccharide, oligosaccharide, cellulose, polyphenol, or lipid. The crosslinker is selected from the group consisting of ingredients reactive with amine, carboxyl, hydroxyl, and thiol functionality such as epoxy, azetidinium, isocyanate, oxazoline or anhydride.

The pre-reacted natural material is present in particles of the invention in an amount effective to improve the barrier properties and environmental biodegradability of the membrane. The amount of pre-reacted natural material resin on a dry basis (weight of pre-reacted natural material resin per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the organofunctional silane as at least one member selected from the group consisting of alkoxylated silane, trialkoxy silanes, functionalized trialkoxysilanes (amino, glycidoxy, methacryloxy, vinyl), tetraalkoxylated silanes including tetramethoxy silane and tetraethoxy silane, 1,2-bis(triethyxysilyl)ethane.

The organofunctional silane is present in particles of the invention in an amount effective to hydrolyze in water and react with the amine moiety to create Si—O—Si bonds. The amount of amine on a dry basis (weight of organofunctional silane per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates. Exemplary isocyanates are selected from the group consisting of hexamethylene diisocyanates (Desmodur N3600, Desmodur N3800, Desmodur N3900, Desmodur N3200, Desmodur N3300, Desmodur N3400, Takenate D-170N), isophorone diisocyanates (Desmodur XP2565, Desmodur Z4470), blends of hexamethylene diisocyanate and isophorone diisocyanate (Desmodur XP2847, Desmodur XP2489, Desmodur XP2838, Desmodur XP2763), pentane-1,5-diisocyanate (Stabio D-370N, Stabio D-376N), xylylene diisocyanate (Takenate 500, Takenate 600, Takenate D-110N, Takenate D-131N), polymeric methylene diphenyl diisocyanate (Mondur MR Lite), polymeric MDI (Desmodur VK 5, Desmodur VL R10, Desmodur 44V40L, Desmodur 44V70L), polyether modified hydrophilic polyisocyanates (Bayhydur XP2451/1, Bayhydur XP2547, Bayhydur XP2759, Bayhydur Ultra 304, Bayhydur Ultra 2487/1), CN9302, ionically modified isocyanates (Bayhydur 2858 XP, Bayhydur XP2759, Bayhydur eco 7190), and the like.

In certain embodiments the epoxy is at least one member selected from the group consisting of epoxidized unsaturated oils such as epoxidized soybean oil, epoxidized vegetable oil, and the like; epoxidized alcohols such as isoborbide glycidyl ether, polyglycerol-3-glycidyl ether, castor oil glycidyl ether; epoxidized polysaccharides such as sorbitol polyglycidyl ether, EX-201: Resorcinol Diglycidyl Ether; EX-211: Neopentyl Glycol Diglycidyl Ether; EX-212: 1,6-Hexanediol Diglycidyl Ether; EX-252: Hydrogenated Bisphenol A Diglycidyl Ether; EX-313: Glycerol Polyglycidyl Ether; EX-314: Glycerol Polyglycidyl Ether; EX-321: Trimethylolpropane Polyglycidyl Ether; EX-411: Pentaerythritol Polyglycidyl Ether; EX-421: Diglycerol Polyglycidyl Ether; EX-512: Polyglycerol Polyglycidyl Ether; EX-612: Sorbitol Polyglycidyl Ether; EX-711: Diglycidyl Terephthalate; EX-721: Diglycidyl o-Phthalate; EX-731: N-Glycidyl Phthalimide; EX-810: Ethylene Glycol Diglycidyl Ether; EX-811: Ethylene Glycol Diglycidyl Ether; EX-850: Diethylene Glycol Diglycidyl Ether; EX-851: Diethylene Glycol Diglycidyl Ether; EX-821: Polyethylene Glycol Diglycidyl Ether; EX-920: Polypropylene Glycol Diglycidyl Ether; EM-160: Emulsion of Epoxy Cresol Novolac Resin; DENA-COL FCA-640: Hexahydrophthalic acid diglycidyl ester; and the like, available from Nagase.

The epoxy is present in particles of the invention in an amount effective to react with the amine moiety, the isocyanate moiety, and/or the hydrolyzed organofunctional silane moieties. The amount of epoxy on a dry basis (weight of epoxy per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments the at least one epoxide curing agent is at least one member selected from the group consisting of metal chelates, tertiary amines and quaternary amine salts. Suitable materials include triethylamine, triethanolamine, N, N, dimethyl benzylamine, benzyltriethylammonium hydroxide, tetraethylammonium bromide, tetrabutylammonium bromide, iron acetoacetate, aluminum acetoacetate, zinc acetoacetate benzimidazole, 2-ethyl imidazole, tetramethyl guanidine, chromium (III) triethyl hexanoate.

The epoxide curing agent is present in particles of the invention in an amount effective to accelerate epoxy reactivity with amine moiety, hydroxyl moiety or carboxylic acid and/or the hydrolyzed organofunctional silane moiety. The amount of epoxide curing agent on a dry basis (weight of epoxide curing agent per weight of dry matter in the suspension) can be, e.g., from 0.01 wt. % or 0.02 wt. % or 0.03 wt. % or 0.05 wt. % to 0.7 wt. % or 1.0 wt. % or 1.8 wt. %.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligomers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof; polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, 1H-Imidazolium, 1-ethenyl-3-methyl-, chloride, polymer with 1-ethenyl-2-pyrrolidinone, polyamines, polysaccharides with cationic modification, and mixtures thereof. Polysaccharides can be employed with cationic modification and alkoxycationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The deposition aid is present in the controlled release particles in an amount on a dry basis (weight of deposition aid per weight of dry matter in the suspension) from 0.5 wt. % or 1 wt. % or 1.5 wt. % or 3.5 wt. % to 5 wt. % or 7 wt. % of the weight of the particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles according to the present teaching are made in a multi-step process as described below. For convenience, the process is presented in the preferred mode which involves one aqueous phase composition and one hydrophobic oil phase composition. Nonetheless, those skilled in the art will readily appreciate that the aqueous phase composition may be prepared as a dual phase composition to which the hydrophobic oil phase composition is added or a three or more components composition where various ingredients are preferably isolated from one another until desired so as to avoid undue or undesired activation of the aqueous phase monomers or oligomers.

A third aspect of the invention is a method of preparing a composition comprising controlled release particles, said method comprising the sequential steps of:
(a) preparing an oil phase, wherein the oil phase comprises:
  (i) at least one hydrophobic active ingredient, and at least one ethylenically unsaturated monomer or free radical initiator; or
  (ii) at least one hydrophobic active ingredient, at least one ethylenically unsaturated monomer and free radical initiator and optionally one or more of the following compounds: an isocyanate, an epoxy, an organofunctional silane, an epoxide curing agent, a plasticizer and an inorganic solid particle;
(b) preparing an aqueous phase comprising a modified biopolymer, and optionally an emulsifier, buffer, ionic strength modifier or water soluble free radical initiator;
(c) combining the oil phase and the aqueous phase to emulsify the at least one hydrophobic active ingredient to provide an aqueous suspension of the at least one hydrophobic active ingredient;
(d) heating the aqueous suspension; and
(e) adding structuring agents to the aqueous suspension to provide the controlled release particles homogeneously suspended in an aqueous dispersion.

In certain embodiments, step (d) may be conducted at room temperature for several hours before increasing temperature of the aqueous suspension to 60° C. or higher and reacting for 2 to 5 hours.

The hydrophobic oil phase composition is formed by combining the hydrophobic active core material with oil soluble monomers and oligomers. Most preferably this is conducted under moderate increased temperature so as to facilitate the solubilization or suspension of the monomers, oligomers, and other ingredients that may be present, including nucleating agents, in the core material. This is particularly useful if the core material is a solid or wax or a high viscosity material. Once again, if the temperature of the mixture had been elevated to aid in getting the hydrophobic oil phase monomer into solution/suspension, then the mixture should be cooled or allowed to cool to ambient temperature.

Materials that are not necessarily soluble or miscible in the oil phase can also be dispersed in the oil phase. The purpose is to maintain these materials at the oil-water interface to improve the properties of the membrane. In the invention, polysaccharides, inorganic solid particles, basified biodegradable resins, pre-reacted natural material resin, and plasticizers are often materials that are not miscible in oil; however, they influence the barrier properties, flexibility, and biodegradability properties of the membrane.

Plasticizers are preferably polymeric in nature, having a molecular weight greater than 1000 Daltons, and are preferably methyl esters of rosin, polyazelate esters, di-fatty acid esters, citrate esters, polyadipate esters, and polyester resins consisting of inner and intra-esters of polyhydroxy carboxylic acids The hydrophobic oil phase composition is added to an aqueous phase to form an emulsion. The mixture is agitated until the desired droplet size of oil phase composition is attained. Droplets are preferably from about 10 microns to about 75 microns, and more preferably from about 20 microns to about 50 microns in volume average diameter.

The aqueous phase, in part, contains a modified biopolymer of the invention. The modified biopolymer provides desirable biodegradability while also providing stability to the initially formed droplets of hydrophobic actives. As the modified biopolymer polymerizes, the droplet surface hardens into the finished capsule.

Polymerization of the membrane is generally conducted at temperatures below 70° C. particularly when encapsulating fragrance (to minimize loss of fragrance notes) or temperature sensitive materials. However, choice of reaction temperature is dependent on both the stability of biopolymer as well as hydrophobic active in general. The reaction time is dependent on the reaction temperature and choice of initiator system but is typically 0.5 hrs to 8 hrs.

Inventors have discovered that pursuing a uniform high degree of crosslinking in making the capsule membrane by chemical reaction processes with synthetic (e.g. polyurea, polyurethane, polyester, polyamide and the like) or even biodegradable natural materials may provide a membrane with good barrier properties and mechanical properties but such membranes have poor environmental biodegradability. Not to be limited by theory, a uniformly high degree of crosslinking results in the absence of the necessary functional groups and needed flexibility that hinder the ability of both water and microbes to permeate onto or within a membrane surface to start degradation processes. On the other hand, a low degree of crosslinking may provide good degradability but often poor mechanical properties and high permeability properties of the membrane.

The modified biopolymer of the invention attempts to circumvent the tradeoffs inherent in the prior art by encouraging non-uniform, high crosslink densities in regions of the membrane while limiting the overall number of linkages per biopolymer backbone. The locally high crosslink density improves overall mechanical performance of the membrane yet enough flexibility and hydrophilicity is retained to aid degradation. Further, due to the high degree of unsaturation in the modified biopolymer, crosslinking between biopolymer backbones is encouraged thus improving mechanical and barrier properties.

Incorporation of biodegradable materials into the membrane via the use of pre-reacted natural material resin can further improve barrier properties of the membrane (more tortuous path for the encapsulated material to diffuse, poor miscibility of the encapsulated active material in the polymer, biodegradable polymer segments swell with water reducing the diffusion of the encapsulated active.

In certain embodiments, the suspension of controlled release particles is dehydrated in order to expose the particles to a higher temperature to achieve a higher degree of crosslinking of the monomers.

In certain embodiments of providing a powder composition of the invention, or making the dehydrated forms of basified biodegradable resin, or making the pre-reacted natural material resin, spray drying is an economical process that can be used. Spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

In certain powder composition embodiments, the silica flow aid is added to the dry powder to improve the flowability of the powder. Addition of the silica flow aid minimizes the agglomeration of particles during the heating, packing, and conveyance processes.

Advantages of at least some embodiments of the inventive method include at least one or at least two or at least three or at least four or at least five or at least six or all seven of the following:

a) Flexibility in choice of active ingredient: membrane is developed at the oil-water interface via the use of interfacial polymerization;
b) Controlled permeability of the shell;
c) Controlled aggregation of the particles;
d) Functionalized surface to increase the adhesion or filtration efficiency of particles onto the substrate during a rinse-off process;
e) Favorable environmental biodegradability profile;
f) Can be used in a variety of applications, including but not limited to household care, personal care, beauty care, etc.; and/or
g) Preferably utilizes a commercially available, relatively inexpensive technique to further engineer the particle.

Compositions Containing the Particles

The invention further comprises compositions (e.g., products, articles of manufacture, etc.) comprising the controlled release particles. Such compositions include but are not limited baby care, beauty care, fabric & home care, family care, feminine care, health care, snack and/or beverage products or devices intended to be used or consumed in the form as sold, and not intended for subsequent commercial manufacture or modification. Such products include but are not limited to fine fragrances (e.g., perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 sec$^{-1}$ shear rate and at 21° C., of from 1 to 7000 cps and a low shear viscosity, at 0.5 sec$^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, gelatin, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry comprising particles of the invention. Said slurry may be combined with an adjunct ingredient to form a composition, for example, a consumer product. In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose and cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol, non-polar solvents including but not limited to mineral oil, perfume raw materials, silicone oils, hydrocarbon paraffin oils, and mixtures thereof.

In certain embodiments, a perfume oil is combined with the slurry comprising microcapsules to provide multiple benefits. The emulsified perfume oil will increase the viscosity of the slurry and prevent the phase separation of the microcapsule particles. The mixture provides a way to deliver non-encapsulated and encapsulated fragrance from the same slurry.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the invention is not deemed to be limited thereto.

EXAMPLES

Materials and Methods

The following is a representative perfume oil composition used for capsule making.

TABLE 1

Perfume oil composition

| Material | wt % | Functionality |
|---|---|---|
| CITRONELLYL NITRILE | 1.00% | NITRILE |
| TRIPLAL | 0.25% | ALDEHYDE |
| FLORHYDRAL | 0.10% | ALDEHYDE |
| ALDEHYDE C-10 | 0.10% | ALDEHYDE |
| ALDEHYDE C-12 LAURIC | 0.20% | ALDEHYDE |
| ALLYL CYCLOHEXYL PROPIONATE | 1.00% | ESTER |
| CETALOX | 0.20% | FURAN |
| ANISIC ALDEHYDE | 0.10% | ALDEHYDE |
| CYCLACET | 10.00% | ESTER |
| CYCLAPROP | 5.00% | ESTER |
| DIHYDROMYRCENOL | 10.00% | ALCOHOL |
| DIPHENYL OXIDE | 1.00% | OXIDE |
| HABANOLIDE | 2.50% | KETONE |
| YARA YARA | 2.00% | ETHER |
| CIS-3-HEXENYL SALICYLATE | 2.00% | ESTER |
| VERDOX | 2.50% | ESTER |
| HEXYLCINNAMIC ALDEHYDE | 20.00% | ALDEHYDE |
| BHT | 0.50% | 0.0025 |
| ISO E SUPER | 2.50% | KETONE |
| KOAVONE | 2.50% | 0.0625 |
| EUCALYPTOL | 0.20% | ALCOHOL |
| MANZANATE, 10% IPM | 0.50% | ESTER |
| MUSCENONE, 10% IPM | 0.50% | KETONE |
| LAEVO CARVONE, 10% IPM | 0.50% | 0.0025 |
| METHYL ANTHRANILATE | 0.10% | ESTER |
| METHYL IONONE GAMMA | 1.25% | KETONE |
| LILIAL | 10.00% | ALDEHYDE |
| ALDEHYDE C-12 MNA, 10% DPG | 0.50% | ALDEHYDE |
| MYRAC ALDEHYDE | 0.50% | ALDEHYDE |
| D-LIMONENE | 5.00% | TERPENE |
| PEONILE | 2.50% | NITRILE |
| ETHYLENE BRASSYLATE | 12.50% | ESTER |
| PHENOXANOL | 2.50% | ALCOHOL |

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of liquid detergent added to 99 grams of water, then filtered through Whatman 597 filter catalog number 10311808) is added powder or slurry that achieves a concentration of approximately 1 wt. % perfume oil in the detergent solution. For water solubility, the powder is simply dosed into water rather than detergent solution. For the Detergent Dissolution Test, the sample is mixed at 200 RPM for 30 minutes at 33.3° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are two techniques utilized to evaluate odor of fabrics:

1) The dried fabrics from the Detergent Dissolution Test+Fabric Preparation test are evaluated olfactively by a panel before and after rubbing. A subjective grading scale is used to grade fabrics before rubbing and after rubbing. In the case of before rubbing, the control that is used is a fabric treated with neat fragrance oil in the detergent solution. In the case of rubbed fabric, the control is the fabric before rubbing is performed.

TABLE 2

Odor grading scale

| Odor Grade | Description |
|---|---|
| 0 | No Difference vs. Control |
| 1 | Slight Difference vs. Control |
| 2 | Noticeable Difference vs. Control (detectable difference) |
| 3 | Significant difference vs. control (high intensity vs. control) |
| 4 | Very High Intensity Bloom vs. control |
| 5 | Extremely High Intensity vs. Control |

The dried fabrics from the Detergent Dissolution Test+Fabric Preparation test are evaluated by an Odor Meter (Shinyei Technology model OMX-SRM) before and after rubbing. This method reports the total concentration of volatiles in the headspace and is reported in milligrams per cubic meter as a function of time Free Oil Approximately 0.20 grams to 0.27 grams of microcapsule slurry is preweighed in a 20 mL glass scintillation vial. 10 mL of hexane is added to the slurry. The scintillation vial is overturned 10 times to allow for mixing. The scintillation vial is then placed on a platform shaker that shakes the vial at a frequency of 1/sec to allow for mixing of the contents, for 10 minutes. The scintillation vial is allowed to sit unagitated at room temperature for 10 minutes. Sodium sulfate or sodium chloride could be added if there is a lack of phase separation of the hexane layer observed. Approximately 3 mL of the clear hexane layer is removed, placed into a syringe filter (0.45 micron, 25 mm diameter Acrodisc PTFE filter), and decanted into a GC vial. The sample is analyzed by Gas Chromatography. GC conditions are shown in Table 3 below.

TABLE 3

| GC CONDITIONS |
|---|
| Oven |

Initial Temperature: 40° C.
Rate: 5° C./min to 250° C.
Hold Time at Inlet Temp: 2 minutes
Run Time: 44.00 minutes TABLE 3-continued

GC CONDITIONS

Inlet

Mode: Split
Split Ratio: 8:1
Initial Temperature: 240° C.
Column Flow: 1.2 mL/min (constant flow mode)
Column Type: DB-5, 30 m, 0.25 mm duameter, 0.25 μm film thickness
Basic MSD Settings Low Mass: 50
High Mass: 550
Threshold: 500
MS Quad Temperature: 150° C.
MS Source Temperature: 230° C.
Transfer Line Temperature: 250° C.

Biodegradability

Biodegradability testing is carried out according to protocol OECD 301D. The microcapsule membrane is isolated by going through the following steps: (1) dilute the microcapsule slurry 1:10 with water (2) centrifuge the slurry at 5000 RPM to isolate the capsules and remove all water soluble materials, (3) repeat these steps 3 times, (4) dry the isolated capsules in a vacuum oven at 25° C. for 48 hours, (5) mill the powder using ceramic beads, (6) toluene extraction of the milled powder, followed by filtration to recover the particles, 7) vacuum drying of the powder to remove residual toluene at 0.3 torr for 2 days at 25° C., (7) repeat milling of the powder using ceramic beads, (8) water extraction of the milled powder to remove any water soluble components in the membrane, followed by filtration to recover the particles, 9) vacuum dry the powder to remove residual oil at 0.3 torr for 1 day at room temperature. In order to assure that residual oil has been removed, perform hexane extraction followed by Gas Chromatography analysis on the dried powder to assure less than 5% residual oil. The isolated polymer is then subjected to OECD 301D protocol, available at www.oecd.org/chemicalsafety/risk-assessment/1948209.pdf, with the following experimental conditions:

1) test substance concentration in the mineral medium is 5 mg/L
2) 300 mL BOD bottles with glass stoppers are used
3) An incubator at 20 C is used to age the samples in the dark
4) The mineral stock solutions as provided in the method are prepared
5) The inoculum comprises Interlab Polyseed seed BOD inoculum tablets. Such tablets are EPA accepted, non-pathogenic, free of nitrifying microorganisms. 1 capsule is mixed with 0.5 L of APHA standard dilution water at 20 C, and stirred for 60 minutes.
6) COD of the isolated polymer is measured using Hach kit The bottles are checked for dissolved oxygen at 0 days, 7, 14, 21, and 28 days. The percent degradation is analyzed via the calculations taught in the OECD 301D method.

Example 1—Maltodextrin Modification

Twenty (20) grams of maltodextrin (DE 4, Grain Processing Corp) is dissolved in 80 g DMSO and heated to 95° C. Vacuum is gradually applied (max vacuum is ~28 mmHg) and 20 ml of Dimethyl Sulfoxide is removed and the maltodextrin solution is cooled. 12.5 g of maltodextrin solution is diluted with 2.5 g dry Dimethyl Sulfoxide and, with stirring, 5.34 g of an inhibited reaction product of Tert-butyl acetoacetate and trimethyolpropane triacrylate (Sartomer USA LLC) is added. The batch is heated for 2 hrs at 120° C. under nitrogen inertion. The batch is cooled and precipitated with 50 g of MTBE. The precipitate is redissolved in ~7 g water and then reprecipitated with ~30 g Isopropyl Alcohol. The precipitate is redissolved in water and is distilled under vacuum at 40° C. to remove residual volatiles. The pH is adjusted with dilute sodium hydroxide to pH 7.7. Final solids of the clear aqueous solution is 24.9%.

Example 2

Twenty grams (20) of pectin (Herbstreith) is added in 4 equal shots to 80 g water containing 50 ppm of Copper Chloride at 85° C. With each pectin addition, 4 drops of hydrogen peroxide (30%) are added and the batch was held at temperature for 10 minutes before the next addition. After the last hold, an additional 16 drops of hydrogen peroxide (30%) are added and the batch was held at 85° C. for 15 minutes before cooling to room temperature. Five (5) grams of the pectin solution is placed in a vial and 1.43 g of an acetone solution of an oxazoline functional diacrylate modifier (39.1% actives) was added with mixing. The vial is placed in a water bath at 60° C. for 20 minutes and then removed and cooled to room temperature to prepare the aqueous modified pectin solution.

Example 3

To 1.12 g of fragrance oil is added 0.0015 g Vazo 52, 0.0066 g trimethyolpropane triacrylate (Sartomer USA LLC) and 0.0233 g methyl methacrylate. 0.5 g of modified Maltodextrin solution of Example 1 is added followed by 4.23 g water. The mixture is homogenized at 9000 rpm for 1 minute (Ultra Turrax,). A magnetic stirrer is added and the homogenized mixture is placed in a water bath at 65° C. with agitation. The batch is held at 65° C. for 4.5 hours and then cooled to form the final biodegradable slurry.

Example 4

To 1.06 g of fragrance is added 0.0022 g Vazo 52, 0.0022 g Norox 600, 0.0062 g Methyl methacrylate and 0.0013 g Methyl Acrylate to form a fragrance mixture. An aqueous solution consisting of 0.48 g of pectin solution from Example 2, 1.58 g water and 4.75 g of a 20% sodium chloride solution is mixed and the fragrance mixture is added. The combined mixture is homogenized at 13,000 rpm for 1 minute (Ultra Turrax). A magnetic stirrer is added and the homogenized mixture is placed in a water bath at 65° C. with agitation. The batch is held at 65° C. for 4.5 hours and then cooled to form the final biodegradable slurry Example 5

To 1.06 g of fragrance is added 0.0022 g Vazo 52, 0.0022 g Norox 600, 0.0059 g Methyl methacrylate and 0.0031 g Methyl Acrylate to form a fragrance mixture. An aqueous solution consisting of 0.50 g of pectin solution from Example 2, 1.58 g water and 4.75 g of a 20% sodium chloride solution is mixed and the fragrance mixture is added. The combined mixture is homogenized at 11,000 rpm for 1.5 minute (Ultra Turrax). During homogenization, 0.963 g of a 10% aqueous gelatin (Gelita) solution and 0.08 g of a 1% Hydrogen Peroxide solution is added. A magnetic stirrer is added and the homogenized mixture is placed in a water bath at 65° C. with agitation. The batch is held at 65° C. for 4.5 hours and then cooled to form the final biodegradable slurry.

Example 6

To 1.06 g of fragrance is added 0.0022 g Vazo 52, 0.0022 g Norox 600, 0.035 g Methyl methacrylate and 0.0018 g Methyl Acrylate to form a fragrance mixture. An aqueous solution consisting of 0.50 g of pectin solution from Example 2, 1.58 g water and 4.75 g of a 20% sodium chloride solution and 0.092 g of a 2% Methylene Bisacrylamide solution is mixed and the fragrance mixture is added. The combined mixture is homogenized at 11,000 rpm for 1.5 minute (Ultra Turrax). During homogenization, 0.642 g of a 10% aqueous gelatin (Gelita) solution and 0.08 g of a 1% Hydrogen Peroxide solution are added. A magnetic stirrer is added and the homogenized mixture is placed in a water bath at 65° C. with agitation. The batch is held at 65° C. for 4.5 hours and then cooled to form the final biodegradable slurry.

Example 7

To 9 g of fragrance are added 0.0382 g Vazo 52, 0.214 g Methyl methacrylate and 0.143 g Vinyl Pyridine to form a fragrance mixture. An aqueous solution consisting of 4.25 g of pectin solution from Example 2, 13.47 g water and 40.41 g of a 20% sodium chloride solution and 0.782 g of a 2% Methylene Bisacrylamide solution is mixed and the fragrance mixture is added. The combined mixture is mixed at 900 rpm with an overhead pitched blade agitator and heated to 65 C. At 55 C, 5.45 g of a 10% aqueous gelatin (Gelita) solution and 0.68 g of a 1% Hydrogen Peroxide solution is added. The batch is held at 65° C. for 4.5 hours and then cooled to form the final biodegradable slurry Example 8. Leakage Stability Testing Microcapsules slurries are formulated into liquid fabric softener (Downy Free & Clear, market product) to deliver approximately 0.5 wt % fragrance usage level in the liquid suspension, via the microcapsules or neat perfume oil. The mixtures are aged for 1 week at 40° C. After ageing, several tests are performed to evaluate the behavior of the capsules
1) Optical microscopy to observe capsule deflation
2) Approximately 5 grams of the detergent mixture is diluted with 5 grams of water to yield a dilute detergent solution containing approximately 0.25 wt % fragrance oil. Next, approximately 2 mL of the mixed solution is filtered through a black fabric, and allowed to dry at 70° C. for 1 hour. The fabric odor intensity before rubbing and after rubbing is noted.

TABLE 5

Fabric odor performance of microcapsule slurries aged in liquid fabric softener for 1 week at 40° C.

| ID | Description of Capsule (0.5 wt % Floral Fresh in Downy Fabric Softener) | Det Diss Test Pre-Rub/ Post-Rub | Leakage 1 wk/ 40° C. | Leakage 4 wk/ 40° C. |
|---|---|---|---|---|
| Example 3 | Modified maltodextrin particle | 0/3 | 21% | 22% |
| Example 4 | Modified pectin particle | 0/3 | 14.8% | 15.8% |

| Performance Grading Scale | |
|---|---|
| Pre-Rub or Post-Rub Odor Grade | Description |
| 0 | No odor |
| 1 | Slight odor |
| 2 | Noticeable odor |
| 3 | Highly Noticeable, obvious odor |
| 4 | Strong and highly impactful odor |

Example 9. Environmental Biodegradability

Microcapsules of various examples above were evaluated for environmental biodegradability by adapting the OCDE/OECD 301D Closed Bottle Test method, as described in the Biodegradability test method description.

TABLE 6

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dehydrate | $Na_2HPO_4-2H_2O$ | 33.40 |
| | Ammonium chloride | $NH_4Cl$ | 0.50 |
| | Dissolve in water and bring to 1 L. pH to 7.4 | | |
| B | Calcium Chloride anhydrous OR | $CaCl_2$ | 27.50 |
| | Calcium Chloride dehydrate | $CaCl_2-2H_2O$ | 36.40 |
| | Dissolve in water and bring to 1 L. | | |
| C | Magnesium sulfate heptahydrate | $MgSO_4-7H_2O$ | 22.50 |
| | Dissolve in water and bring to 1 L. | | |
| D | Iron (III) chloride hexahydrate Dissolve in water and bring to 1 L. | $FeCl_3-6H_2O$ | 0.25 |

To 996 mL of the APHA standard dilution water is added 2 polyseed BOD tablets, followed by addition of 1 mL each of mineral solutions A, B, C, and D. Prepare approximately 300 mL solutions containing the particles to be tested (approximately 1.5 milligrams of the isolated polymer is added to each BOD bottle). Fill BOD bottles (300 mL capacity) just past the neck of the bottle. Insert stopper. Store BOD bottles in the dark in an incubator maintained at 20° C.

Use dissolved oxygen meter (YSI 5000), and YSI5905 Dissolved Oxygen meter probe to measure oxygen at specific time points.

The dissolved oxygen measured values as a function of time, and the calculation methods presented in OECD 301D method are utilized to calculate the % biodegradability. The Environmental Biodegradability index is calculated by multiplying the measured % biodegradability by 100. The results are listed in Table 7 below.

TABLE 7

Environmental Biodegradability Results

| | Attribute | |
| --- | --- | --- |
| Material | OECD 301D % Biodegradability (60 day) | Biodegradability Index |
| Example 3 | 32% | 32 |
| Example 4 | 31% | 31 |

Example 10—Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of Examples 3 to 7, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 10.1 below.

TABLE 10.1

Hair Condition Formulation

| Components | Ex. I (LOT) (%) |
| --- | --- |
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 11—Shampoo

Selected microcapsules from the above examples are formulated into a rinse-off shampoo formulation as follows: to 90.0 grams of shampoo formulation is added an appropriate amount of microcapsule slurry of Examples 3 to 7, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 11.1, 11.2 and 11.3 below.

TABLE 11.1

Shampoo Formulations of Examples 11A-11C.

| | Example | | |
| --- | --- | --- | --- |
| Ingredient | 11A | 11B | 11C |
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsules | 1.2 | 1.2 | 1.2 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW—500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 11.2

Shampoo Formulations of Examples 11D-11F.

| | Example | | |
| --- | --- | --- | --- |
| Ingredient | 11D | 11E | 11F |
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.2 | 1.2 | 1.2 |

[1] Glycidol Silicone
[4] Cyclopentasiloxane: SF1202 available from Momentive Performance Chemicals
[5] Behenyl trimethyl ammonium chloride/Isopropyl alcohol: Genamin TM KMP available from Clariant
[6] Cetyl alcohol: Konol TM series available from Shin Nihon Rika
[7] Stearyl alcohol: Konol TM series available from Shin Nihon Rika
[8] Methylchloroisothiazolinone/Methylisothiazolinone: Kathon TM CG available from Rohm & Haas
[9] Panthenol: Available from Roche
[10] Panthenyl ethyl ether: Available from Roche

TABLE 11.3

Shampoo Formulations of Examples 11G and 11H

| Ingredient | Example 11G | Example 11H |
|---|---|---|
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride [1] | 0.40 | |
| Guar Hydroxypropyl trimonium chloride [2] | | 0.40 |
| Dimethicone [3] | 2.00 | 2.00 |
| Gel Network [4] | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

[1] Jaguar C17 available from Rhodia
[2] N-Hance 3269 (with Mol. W. of ~500,000 and 0.8 meq/g) available from Aqulaon/Hercules
[3] Viscasil 330M available from General Electric Silicones
[4] Gel Networks; See composition in Table 14.4 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 11.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 12—Lotion

For the examples shown in Table 12 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 12

Lotion Formulations (Examples 12A-12C).

| Ingredient/Property | Example 15A | Example 15B | Example 15C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO$_2$ | | | 0.50 |
| Iron oxide coated Mica | | | 0.65 |
| TiO$_2$ Coated Mica | 1.00 | 1.00 | |
| Fragrance Microcapsules | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

Example 13—Antiperspirant/Deodorant

Example 13A of Table 13.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 13.1

Antiperspirant/Deodorant Formulation (Example 13A).

| Ingredient | Example 13A |
|---|---|
| Part I: Partial Continuous Phase | |
| Hexamethyldisiloxane[1] | QS |
| DC5200[2] | 1.20 |
| Fragrance | 0.35 |
| Fragrance Capsules | 1.00 |

TABLE 13.1-continued

Antiperspirant/Deodorant Formulation (Example 13A).

| Ingredient | Example 13A |
|---|---|
| Part II: Disperse Phase | |
| ACH (40% solution)[4] | 40.00 |
| propylene glycol | 5.00 |
| Water | 12.30 |
| Part III: Structurant Plus Remainder of Continuous Phase | |
| FINSOLVE TN | 6.50 |

QS—indicates that this material is used to bring the total to 100%.
[1]DC 246 fluid from Dow Corning
[2]from Dow Corning
[3]Standard aluminum chlorohydrate solution Examples 13B to 13E of Table 13.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 13F of Table 13.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 13.2

Antiperspirant/Deodorant Formulations

| | Example | | | | |
|---|---|---|---|---|---|
| Ingredient | 13B | 13C | 13D | 13E | 13F |
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragrance | 0.5 | 0.5 | 0.5 | 0.5 | 0.5 |
| Fragrance capsules | 1.0 | 1.0 | 1.0 | 1.0 | 0.5 |
| Propellant (1,1 difluoroethane) | | | | | 40 |

QS—indicates that this material is used to bring the total to 100%.

Example 14—Rinse-Off Conditioner

The conditioning compositions of Examples 14A through 14F of Table 14 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 14B of Table 14 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 14

Rinse-Off Conditioner Formulations (Examples 14A-14F).

| | Example | | | | | |
|---|---|---|---|---|---|---|
| Ingredient | 14A | 14B | 14C | 14D | 14E | 14F[3] |
| Premix | | | | | | |
| Aminosilicone-1 [1] | 0.50 | 0.50 | | | | |
| Aminosilicone-2 [2] | | | 0.50 | 0.50 | 0.50 | |
| PDMS | | | | | | 0.50 |
| Fragrance microcapsules | . . . | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 mmol/g and a viscosity of 3,000-8,000 mPa · s, which is water insoluble
[2] Aminosilicone-2 (TAS): having an amine content of 0.04-0.06 mmol/g and a viscosity of 10,000-16,000 mPa · s, which is water insoluble
[3]Comparative example with PDMS instead of amino silicone Example 15—Body Cleansing Composition The body cleaning compositions of Examples 15A-15C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The Benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 15

Body Cleansing Composition Formulations (Examples 15A-15C).

| Ingredient | Example 15A | Example 15B | Example 15C |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules | 10 | 10 | 10 |
| III: Surfactant Phase:Benefit Phase Blending Ratio | 50:50 | 90:10 | 90:10 |

Example 16—Fabric Softening Product

Non-limiting examples of product formulations containing purified perfume microcapsules of the aforementioned examples are summarized in the following table.

TABLE 16

Fabric Softening Product Formulations (Examples 16A-16J).

| Ingredient | 16A | 16B | 16C | 16D | 16E | 16F | 16G | 16H | 16I | 16J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |

TABLE 16-continued

Fabric Softening Product Formulations (Examples 16A-16J).

| Ingredient | 16A | 16B | 16C | 16D | 16E | 16F | 16G | 16H | 16I | 16J |
|---|---|---|---|---|---|---|---|---|---|---|
| Deionized Water | Balance | Balance | Balance | Balance | Balance | Balance | Balance | Balance | Balance | Balance |

[a] N,N-di(tallowoyloxyethyl)-N,N-dimethylammonium chloride.
[f] Copolymer of ethylene oxide and terephthalate having the formula described in U.S. Pat. No. 5,574,179 at col.15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON CG available from Rohm and Haas Co. "PPM" is "parts per million."
[j] Gluteraldehyde
[k] Silicone antifoam agent available from Dow Corning Corp, under the trade name DC2310.
[l] Hydrophobically-modified ethoxylated urethane available from Rohm and Haas under the tradename Aculyn™ 44.
*Suitable microcapsules provided in Examples 3 to 7. (Percent active relates to the core content of the microcapsule)

Example 17—Dry Laundry Formulations

Non-limiting examples of product formulations containing purified perfume microcapsules of the aforementioned examples are summarized in the following table.

TABLE 17

Dry Laundry Formulations (Examples 17A-17G)

| | % w/w granular laundry detergent composition Example | | | | | | |
|---|---|---|---|---|---|---|---|
| Ingredient | 17A | 17B | 17C | 17D | 17E | 17F | 17G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxy ethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Examples 3 to 7) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS-as used herein indicates that this material is used to bring the total to 100%.

Example 18—Liquid Laundry Formulations (HDLs)

Non-limiting examples of product formulations containing purified perfume microcapsules of the aforementioned examples are summarized in Tables 18.1, 18.2 and 18.3 below.

TABLE 18.1

Liquid Laundry Formulations (HDLs)

| Ingredient | 18A | 18B | 18C | 18D | 18E | 18F |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxy ethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules of Examples 3 to 7 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 18.2

Liquid Laundry Detergent Formulations

| Ingredient | 18G | 18H | 18I | 18J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |

TABLE 18.2-continued

Liquid Laundry Detergent Formulations

| Ingredient | 18G | 18H | 18I | 18J |
|---|---|---|---|---|
| Bentonite Softening Clay | | 1.0 | | |
| Polyquaternium 10 - Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | | 1.0 |
| Perfume micro capsules (expressed as perfume oil) of Example 3 to 7 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 18.3

Liquid Laundry Detergent Formulations.

| Ingredient | 18K | 18L | 18M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Examples 3 to 7 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 19—Liquid and Gel Detergents

Non-limiting examples of product formulations containing purified perfume microcapsules of the aforementioned examples are summarized in Table 19 below.

TABLE 19

Liquid and Gel Detergent Formulations (% by Weight)

| Ingredient | 19A | 19B | 19C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Examples 3 to 7 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

Example 20—Liquid Unit Dose

The following are examples of unit dosage forms wherein the liquid composition is enclosed within a PVA film. The preferred film used in the present examples is Monosol M8630 76 μm thickness.

TABLE 20

Unit Dose Laundry Cleaner

| | Example | | | | | | | |
|---|---|---|---|---|---|---|---|---|
| | 20A 3 compartments | | | 20B 2 compartments | | 20C 3 compartments | | |
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxy ethane diphosphonic acid | 0.6 | 0.6 | 0.6 | 0.5 | | | 2.2 | |
| Ethylene diamine tetra(methylene phosphonic) acid | | | | | 0.4 | | | |
| Brightener | 0.2 | 0.2 | 0.2 | 0.3 | | 0.3 | | |
| Microcapsules Example 3 to 7 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine)[2] | To pH 8.0 for liquids To RA > 5.0 for powders | | | | | | | |
| Solvents (1,2 propanediol, ethanol), sodium sulfate | To 100 p | | | | | | | |

[1]Polyethylenimine (MW = 600) with 20 ethoxylate groups per -NH.
[2] RA = Reserve Alkalinity (g NaOH/dose)

While the invention has been described in detail and with reference to specific examples thereof, it will be apparent to one skilled in the art that various changes and modifications can be made therein without departing from the spirit and scope thereof.

What is claimed is:

1. A modified biopolymer having the formula A-XY wherein:
   A is a starting material of a polysaccharide selected from the group consisting of tapioca starch, potato starch, corn starch, rice starch, wheat starch, carboxymethyl starch, carboxymethyl chitosan, chitosan oligosaccharide, and octenyl succinic anhydride modified starch;
   X is a first moiety bearing a functionality co-reactive with the starting material A, wherein the first moiety X is selected from the group consisting of t-butyl acetoacetate, t-butyl cyanoacetate, and a Michael adduct of alkyl acetoacetate or alkyl cyanoacetate with ethylenically unsaturated monomer bearing an anhydride functionality, an epoxy functionality, an isocyanate functionality or an oxazoline functionality;
   Y is a second moiety covalently bound to the first moiety X, capable of undergoing free radical polymerization and having an acrylate, methacrylate, styrenic, vinyl ester or vinyl ether bearing at least three ethylenically unsaturated groups;
   the starting material A and the first moiety X are linked covalently through linkages selected from the group consisting of an ester, an amide, a urethane, a urea, a sulfonate ester, a phosphate ester and an ether; and
   a degree of substitution of the starting material A with the first moiety X is less than 0.5 but more than 0.1, and
   wherein the modified biopolymer has an Environmental Biodegradability greater than 30% within 28 days according to OECD 301.

2. The modified biopolymer of claim 1, wherein the starting material A is adjusted to a lower molecular weight before incorporation into the modified biopolymer.

3. A composition comprising controlled release particles, wherein each of the controlled release particles comprises:
   at least one hydrophobic active ingredient; and
   a reaction product of a free radical polymerization of the modified biopolymer of claim 1 and at least one ethylenically unsaturated monomer.

4. The composition of claim 3, further comprising at least one member selected from the group consisting of a free radical initiator, a cationic deposition aid, an isocyanate, an epoxy, an organofunctional silane, an epoxide curing agent, a plasticizer and an inorganic solid particle.

5. The composition of claim 3, wherein the at least one hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

6. The composition of claim 3, wherein the controlled release particles have a diameter from 0.1 microns to less than 200 microns.

7. The composition of claim 3, which is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

8. The composition of claim 3, wherein the composition comprises two different controlled release particles which are friction-triggered release microcapsules which release the at least one hydrophobic active ingredient at different rates due to a difference in shell material friability or core material viscosity.

9. A method of preparing a composition comprising controlled release particles, said method comprising the sequential steps of:
(a) preparing an oil phase, wherein the oil phase comprises:
(i) at least one hydrophobic active ingredient, and at least one ethylenically unsaturated monomer or free radical initiator; or
(ii) at least one hydrophobic active ingredient, at least one ethylenically unsaturated monomer and free radical initiator and optionally one or more compounds selected from the group consisting of: an isocyanate, an epoxy, an organofunctional silane, an epoxide curing agent, a plasticizer and an inorganic solid particle;
(b) preparing an aqueous phase comprising the modified biopolymer according to claim 1, and optionally an emulsifier, buffer, ionic strength modifier or water soluble free radical initiator;
(c) combining the oil phase and the aqueous phase to emulsify the at least one hydrophobic active ingredient to provide an aqueous suspension of the at least one hydrophobic active ingredient;
(d) heating the aqueous suspension; and
(e) adding structuring agents to the aqueous suspension to provide the controlled release particles homogeneously suspended in an aqueous dispersion.

10. The method of claim 9, wherein the free radical initiator is a member selected from the group consisting of azo initiators and alkyl peroxides.

11. The method of claim 9, wherein at least one suspension agent is included in the composition to suspend the controlled release particles, wherein the at least one suspension agent is at least one member selected from the group consisting of a rheology modifier, a structurant and a thickener.

12. The method of claim 11, wherein the at least one suspension agent has a high shear viscosity at, 20 $sec^{-1}$ shear rate and at 21° C., of from 1 to 7000 cps and a low shear viscosity, at 0.5 $sec^{-1}$ shear rate at 21° C., of greater than 1000 cps.

13. The method of claim 11, wherein a finished capsule slurry is a fluid having a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

14. The method of claim 11, wherein the at least one suspension agent is a member selected from the group consisting of polyacrylates, polymethacrylates, polycarboxylates, pectin, alginate, gum arabic, gelatin, carrageenan, gellan gum, xanthan gum, guar gum, hydroxyl-containing fatty acids, hydroxyl-containing fatty esters, hydroxyl-containing fatty waxes, castor oil, castor oil derivatives, hydrogenated castor oil derivatives, hydrogenated castor wax, perfume oil, and mixtures thereof.

15. A composition comprising the controlled release particles prepared by the method of claim 9, each of the controlled release particles comprises: at least one hydrophobic active ingredient; and a reaction product of a free radical polymerization of the modified biopolymer of claim 1 and at least one ethylenically unsaturated monomer.

* * * * *